United States Defensive Publication [19] (H) [11] T993,005

Staniland [43] Apr. 1, 1980

[54] PREPARATION OF AROMATIC FLUORO COMPOUNDS

[75] Inventor: Philip A. Staniland, Tewin Wood, England

[73] Assignee: Imperial Chemical Industries Limited, London, England

[21] Appl. No.: 22,597

[22] Filed: Mar. 19, 1979

[30] Foreign Application Priority Data

Mar. 31, 1978 [GB] United Kingdom ..... 12664/78
Aug. 10, 1978 [GB] United Kingdom ..... 32842/78

[51] Int. Cl.[2] ..... C07C 45/00
[52] U.S. Cl. ..... 260/591

[57] ABSTRACT

The present invention relates to a process for the preparation of 4,4′-difluorobenzophenone. 4,4-difluorobenzophenone may be prepared by diazotization of 4,4′-diamino-diphenylmethane in anhydrous or concentrated aqueous hydrogen fluoride, decomposition of the diazonium fluoride thus produced to yield 4,4′-difluorodiphenylmethane and oxidation of 4,4′-difluorodiphenylmethane to yield 4,4′-difluorobenzophonone.

Thus, according to the present invention, there is provided a process for the preparation of 4,4′-difluorobenzophenone which comprises the following steps:

(1) diazotization of 4,4′-diamino-diphenylmethane in anhydrous or concentrated aqueous hydrogen fluoride to yield a solution of a corresponding diazonium fluoride; and (2) (i) thermally decomposing the diazonium fluoride in the solution thus produced to yield 4,4′-difluorodiphenylmethane and (ii) subsequently oxidizing the 4,4′-difluoro-diphenylmethane to yield 4,4′-difluorobenzophenone.

7 Claims, No Sheets Drawing,

9 Pages Specification

The file of this unexamined application may be inspected and copies thereof may be purchased (849 O.G. 1221, Apr. 9, 1968).